United States Patent [19]

Rose

[11] Patent Number: 4,934,176
[45] Date of Patent: Jun. 19, 1990

[54] METHOD AND APPARATUS TO DETERMINE AMOUNT OF GAS AND SIZE OF GAS VOIDS ENTRAINED IN VISCOUS SUBSTANCES

[76] Inventor: Mitchel Rose, 2940 Lee Blvd., Cleveland, Ohio 44118

[21] Appl. No.: 250,920

[22] Filed: Sep. 29, 1988

Related U.S. Application Data

[63] Continuation-in-part of Ser. No. 221,011, Jul. 18, 1988, abandoned.

[51] Int. Cl.$^5$ .................. G01N 7/14; G01N 33/38
[52] U.S. Cl. ............................ 73/19.1; 73/38; 73/61 R
[58] Field of Search .................. 73/38, 61 R, 19

[56] References Cited

U.S. PATENT DOCUMENTS

| | | | |
|---|---|---|---|
| 2,635,459 | 4/1953 | Gray | 73/19 |
| 2,668,437 | 2/1954 | Patch | 73/19 |
| 2,722,825 | 11/1955 | Meyer | 73/19 |
| 2,823,540 | 2/1958 | Patch | 73/19 |
| 2,892,343 | 6/1959 | Chace | 73/19 |
| 3,184,957 | 5/1965 | Ellis et al. | 73/38 |
| 4,344,316 | 8/1982 | Nasser | 73/19 |

FOREIGN PATENT DOCUMENTS

| | | | |
|---|---|---|---|
| 554502 | 7/1977 | U.S.S.R. | 73/61 R |
| 697929 | 11/1979 | U.S.S.R. | 73/19 |

OTHER PUBLICATIONS

Ivey, D. L. et al., *Air Void Systems in Ready-Mixed Concrete,* In. J. of Materials, JMLSA, vol. 5, No. 2, pp. 492-522, Jun. 1970.

*Primary Examiner*—Tom Noland
*Assistant Examiner*—Joseph W. Roskos
*Attorney, Agent, or Firm*—William N. Hogg

[57] ABSTRACT

A method of determining the amount of air contained in a viscous building material, such as concrete or asphalt, is provided. A sample of the material is placed in a fluid-tight container and a vacuum is pulled. The air will expand causing the material to expand. The amount of expansion is measured, which expansion is a function of the amount of air in the material. Also, a technique is provided for determining the size of the voids caused by the air.

15 Claims, 5 Drawing Sheets

METHOD AND APPARATUS TO DETERMINE AMOUNT OF GAS AND SIZE OF GAS VOIDS ENTRAINED IN VISCOUS SUBSTANCES

This is a continuation-in-part of application Ser. No. 221,011, filed July 18, 1988 and entitled Method and Apparatus To Determine Amount and Size of Gas Entrained In Viscous Substances now abandoned.

BACKGROUND OF THE INVENTION

1. Field of the Invention

This invention relates generally to the measurement of the amount and/or size of gas bubbles entrained in building materials such as concrete and asphalt, while said materials are still in a viscous or pliable state.

2. Prior Art

It is desirable to be able to determine the amount and size of air voids (bubbles) in concrete. With increasing total air content, there is an increase in freeze-thaw durability, workability, pumpability, adhesion, and sulfate resistance, but a decrease in strength. Void size also affects these properties. It is thus desirable to maintain a controlled amount and size of air voids in concrete.

The following prior art techniques are employed to measure the total volume of entrained air in concrete. They all have drawbacks and limitations.

ASTM C138 test determines air content as the difference in weight of a known volume of sample from its theoretical airfree weight. Even a small error in measured parameters (batch proportions, specific gravity, sample volume or sample weight) yields a significant error in results. The necessary parameters are difficult to obtain accurately in the field.

ASTM C231 test entails measuring the volume reduction of the concrete slurry upon application of pressure to a sample. This is accomplished by either measuring the volume change (compression) of the sample, or by measuring the final air pressure after releasing a known quantity of compressed air into the chamber. The test chamber must be rugged and pressure tight, and therefore expensive.

ASTM C173 test measures the volume reduction of the wet concrete upon dispelling the air through the addition of water and alcohol followed by agitation. This method is laborious and occasionally must be repeated due to insufficient air detrainment. Efforts to enhance the air detrainment with vacuum resulted in a more tedious procedure.

The Air-Master Meter is a smaller, plastic version of the ASTM C173 apparatus. It suffers from the same problems as does ASTM C173, but to a lesser extent.

Chase Air Indicator is a much smaller (4 cc volume) version of the ASTM C173 apparatus, for measuring only the mortar portion of concrete. Its results are prone to error due to small sample size, improper separation of the mortar portion, and improper calibration.

The aforementioned methods are limited to concrete specimens. The following technique has been developed to determine total air content of concrete in-place (in-situ).

The thermal method entails pushing a bottomless chamber into the in-place concrete. A heater within the chamber heats the concrete, causing the sample to expand in proportion to its air content, which, in turn, produces a proportionate air pressure rise. The measured air pressure in the chamber is then related to the air content. The accuracy of this test has not been independently verified.

The following techniques have been developed to determine void size, but are not being used by the industry.

The Void Spacing Indicator Method entails dispersing the concrete in water and observing the size of the detrained air bubbles that rise to the surface. The accuracy of the method is very poor.

The vibration method entails vibrating the sample to detrain the air and graphing volume reduction versus time. This method is based on the principle that larger voids rise to the surface faster than small ones. A complex mathematical formula yields void size from the data. The accuracy of this method has not been determined.

Thus, the present tests for measuring entrained air and void size in concrete all have serious limitations.

SUMMARY OF INVENTION

According to the present invention, an improved method and apparatus are provided for determining the volume of gas entrained in a viscous substance, as well as the size of the voids created by the entrained gas. The slurry of material, such as fresh concrete or other matter, is placed into an essentially fluid tight container. A partial vacuum is generated above the viscous material. The entrained gas within the viscous material expands, while still being entrained therein, causing the viscous material to expand. The amount of expansion of the material and the amount of vacuum applied are measured, with the amount of expansion of the material at any given vacuum level being directly proportional to the amount of gas entrained in the material.

Also, the container can be made transparent. The expanded material will have enlarged voids (which, in concrete, are normally microscopic), and these enlarged voids can be examined with the unaided eye through the transparent container. The void sizes, as they are patterned against the inside of the container, can be studied and measured. One can then calculate the original void size from the dilated void size using the equation: original void size=(dilated void size)×(1 Atm)/(Absolute pressure in Atm units).

DESCRIPTION OF THE PREFERRED EMBODIMENTS

The present invention utilizes the observed phenomenon that if a viscous material having gas entrained therein is subjected to a vacuum, the gas will expand, while remaining entrained in the viscous material as voids, causing the entire mass of viscous material to expand. Further, the amount of expansion of the viscous material will be defined by the equation:

$$dV = (P1/P2 - 1) A,$$

where  $dV$ = % expansion of the material;
 $P1$ = absolute pressure before evacuation;
 $P2$ = absolute pressure after evacuation;
 $A$ = % air content by volume.

The invention, in another aspect, relies on observing that as the viscous material expands, the microscopic voids will expand and become visible on the side wall of the container, and if the container (or a portion thereof) is transparent, the voids can be observed and measured for average size and size variation.

All of the embodiments of this invention entail measuring both applied vacuum and the resulting expansion, and then calculating air content with the equation $dV = (P1/P2 - 1) A$, mentioned above. In practice, one can measure the expansion at a specified vacuum, or measure the vacuum at a specified expansion. The embodiments of FIGS. 1–4 can be used either way, but the embodiment in FIG. 5 can be used only for measuring vacuum at a specified expansion.

Figure 1:
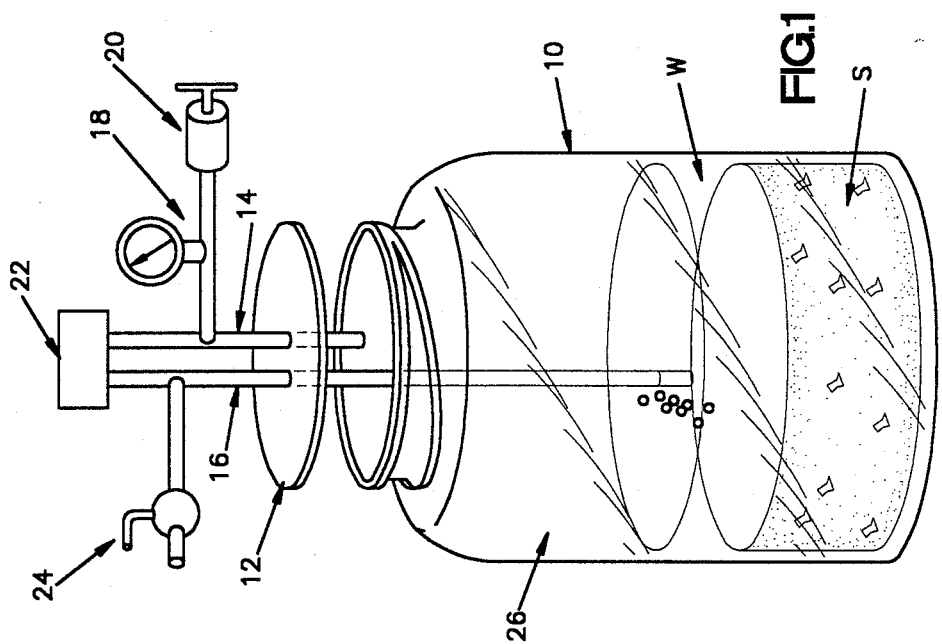
FIG. 1 is a perspective, exploded view of one embodiment of a device for measuring gas content and void size according to this invention.

Referring now to FIG. 1, one embodiment of an apparatus for determining the amount of gas entrained in a viscous material as well as the size of voids caused thereby is shown. This apparatus is adapted to measure air entrained in concrete, but can be used for other materials as will be readily apparent.

The device includes a transparent container 10, which is provided with a lid 12 which can close the container 10 in an essentially airtight sealing relationship. It has been found that conventional home canning jars with vacuum sealing lids can effectively be used in this invention. A pair of tubes 14 and 16 pass through the lid 12 and are sealed therein. A vacuum is produced with vacuum pump 20 and measured with vacuum gauge 18. The tubes 14 and 16 are connected to an electronic differential pressure sensor 22. The tube 16 is also provided with an air release valve 24.

In order to practice the invention, the sample S of material to be tested, such as concrete, is placed in the bottom of the container and a quantity of water W is added on top of the sample. The lid 12 is put in place such that the tube 14 terminates well above the water line and the tube 16 extends beneath the surface of the water. The vacuum pump evacuates the space 26 above the water W. The lid 12 need not be clamped or screwed down, since the vacuum itself will hold it down and seal it. As the pressure drops in the space 26, the entrained air in the concrete sample S starts to expand, and the total volume of concrete sample S expands. The amount of expansion is defined by the expression: $dV = (P1/P2 - 1) A$, mentioned above. This expansion is translated to an increase in differential air pressure between the tubes 14 and 16, which is measured by the electronic sensor 22. Such sensors are commercially available and need not be described in detail. For accurate results in this embodiment, before the first reading, the tube 16 should be cleaned by applying a small vacuum and then actuating the air release valve 24.

In a modification of this apparatus, the pressure sensor 22 and tubes 14 and 16 can be replaced with a simple graduated rod for visually measuring expansion.

Figure 2:
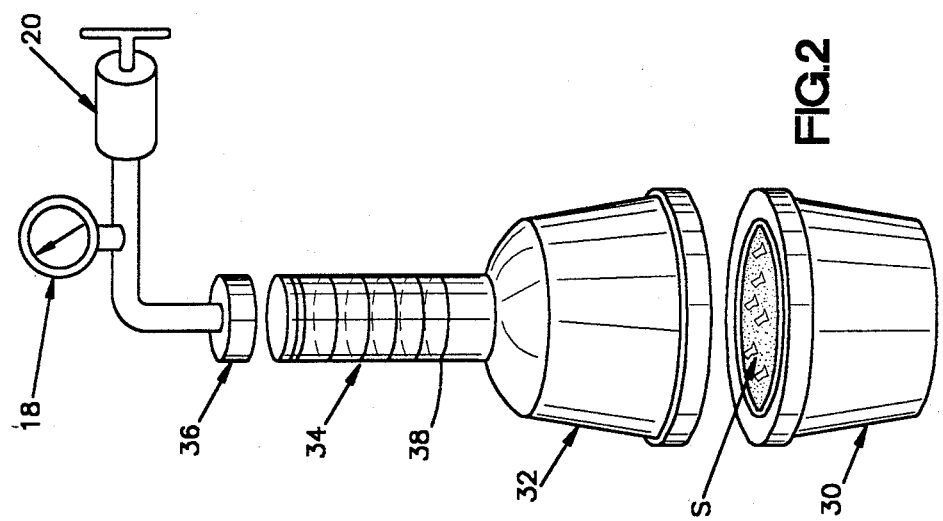
FIG. 2 is a view similar to FIG. 1 of another embodiment of the invention.

FIG. 2 shows yet another device which can be used to measure air entrainment according to this invention. The sample chamber is comprised of a bowl 30 and cap 32 that clamp together with clamps not shown. The cap contains a transparent graduated column 34 and a screw-on cap 36. In this case, the bowl 30 is filled to the top with sample S. The cap 32 is clamped onto the bowl and filled with water up to the first graduation mark 38. Cap 36 is screwed on. A vacuum is produced with vacuum pump 20 and measured with vacuum gauge 18. The expansion of the sample causes the water to rise in the transparent column, and this is visually measured using the column's graduations. Since the water column is thinner than the bowl, vertical displacement of the sample surface produces an amplified displacement of the water surface.

Figure 3:
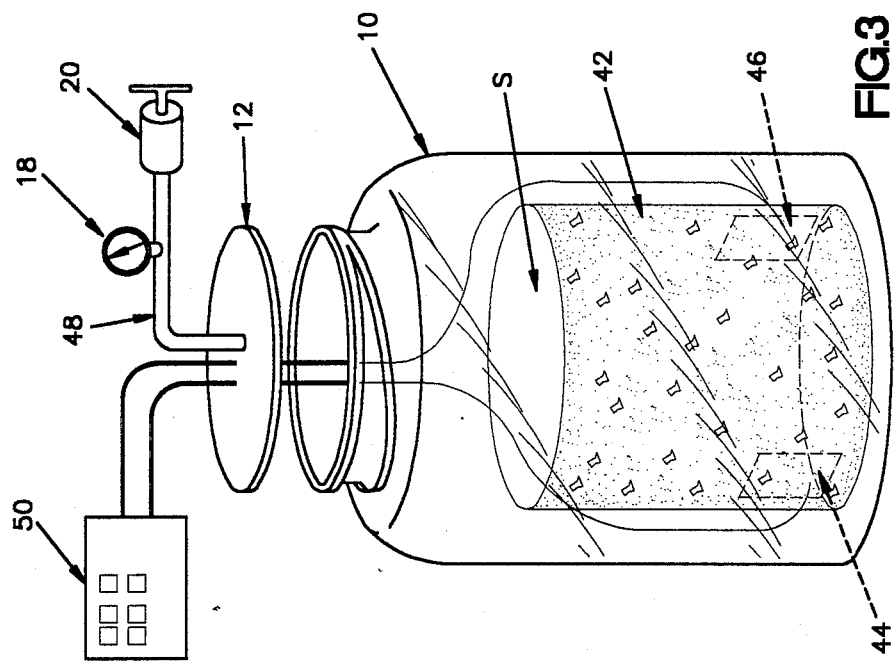
FIG. 3 is yet another embodiment of this invention.

FIG. 3 is another apparatus which can be used to measure gas entrainment according to this invention. In this case, a container 10 and lid 12 are provided just as in the embodiment of FIG. 1. In this case, however, a plastic container 42 is provided in which the sample S of concrete is contained. The container has a pair of spaced electrical conducting plates 44, 46 disposed therein. A vacuum is produced with vacuum pump 20, measured with vacuum gauge 18, and conveyed to the container through tube 48. Conventional electrical circuitry 50 is connected to the two plates 44, 46 to measure the electrical conductivity of the concrete. As the vacuum is applied and the concrete sample S expands, the conductivity of the sample decreases, due to increasing volume of the voids, and the change in resistance is related to the % expansion.

Figure 4:
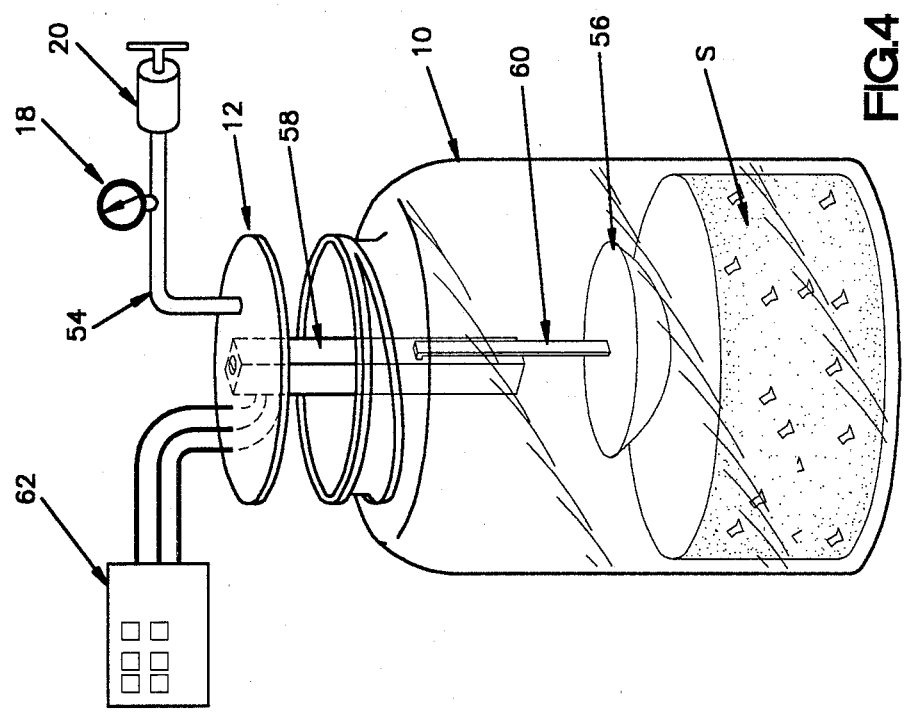
FIG. 4 is still another embodiment of the invention.

FIG. 4 is yet another device for practicing the invention. In this case, a container 10 and lid 12 are provided just as in the previous embodiment. The vacuum is produced by pump 20, measured by gauge 18, and conveyed to the container via tube 54. A float 56 rests on the sample surface and is connected to a slide potentiometer 5 via rod 60. The slide potentiometer 58, fastened to lid 12, is used to measure the displacement of the top surface of the concrete sample S as it expands under vacuum. Commonly available electronic circuitry 62 can be used to display the displacement of the slide potentiometer.

Figure 5:
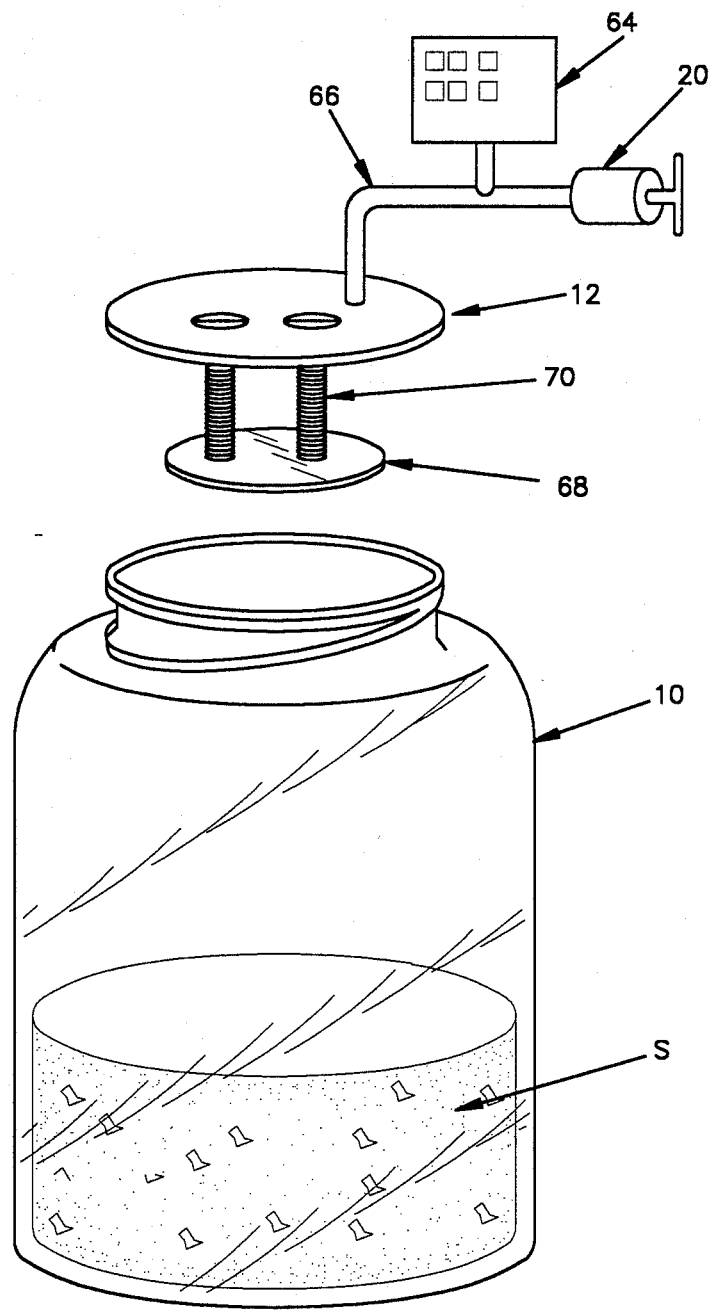
FIG. 5 is still another embodiment of the invention.

FIG. 5 is yet another device for practicing the invention. A transparent container 10 and lid 12 are provided just as in the previous embodiment. The vacuum is produced by pump 20, measured by electronic pressure meter 64, and conveyed to the container via tube 66. A transparent plastic disk 68 is attached below lid 12 with bolts 70. In the procedure, the sample surface rises as the operator gradually evacuates the chamber. The operator records the pressure reading as soon as he observes that the sample surface has contacted the entire disk bottom. In contrast to the other 4 embodiments, here the expansion is not measured per se, but rather is set by the height of the disk above the sample surface.

The sample surface tends to rise faster at the center than at the edge, which would render an ambiguous measurement of expansion. This problem is solved by using a disk 68 instead of a simple rod, since the sample surface will level off as it contacts and presses against the disk, and the operator will record the pressure reading only when he observes the concrete contacting the disk's entire underside.

The procedure for FIG. 5 can be automated by modifying the design in the following way. The pressure meter is provided with a sample-and-hold capability, which freezes the pressure reading upon sensing electrical contact between 2 wires. Those 2 wires are attached to bolts 70, which in turn terminate flush with the bottom of disk 68. In the procedure, the pressure meter will automatically sample-and-hold the pressure reading when the sample surface (which is electrically conductive) contacts the bolts and completes the circuit. For samples that are not electrically conductive, such as asphalt, the sample surface is covered with saltwater.

The apparati of FIGS. 1-5 can be modified to measure air content of in-place concrete by replacing the sample chambers with a cylinder. The cylinder can be considered as a bottomless sample chamber. The procedures are the same as described above, except that the cylinder is pressed into the in-place concrete instead of placing a concrete sample inside the chamber. This method is similar to the thermal method described above, except that this method uses vacuum to expand the sample instead of heat. Advantages of this method over the thermal method are that expansion is quicker and independent of thermal properties of the sample, and requires less electric power.

The apparati of FIGS. 1, 2, 4 and 5 also can be used to measure the air content of asphalt cores and pills with no design modification.

In all of these devices, the % air content is a function of both the vacuum and resulting % expansion. Also, in each case, when the container for the sample S is transparent, the average size and size distribution of voids can be examined. Boyle's law indicates that by evacuation to $\frac{1}{4}$, 1/5, 1/6, 1/7 and $\frac{1}{8}$ atmosphere, the absolute void size increases by the reciprocal, i.e. 4x, 5x, 6x, 7x, and 8x, respectively. Also, at this expanded size, the voids can be compared for variation in size within the sample as well as to other samples. Thus, one need pull a vacuum sufficient only to make all of the voids visible and measurable.

Figure 6:
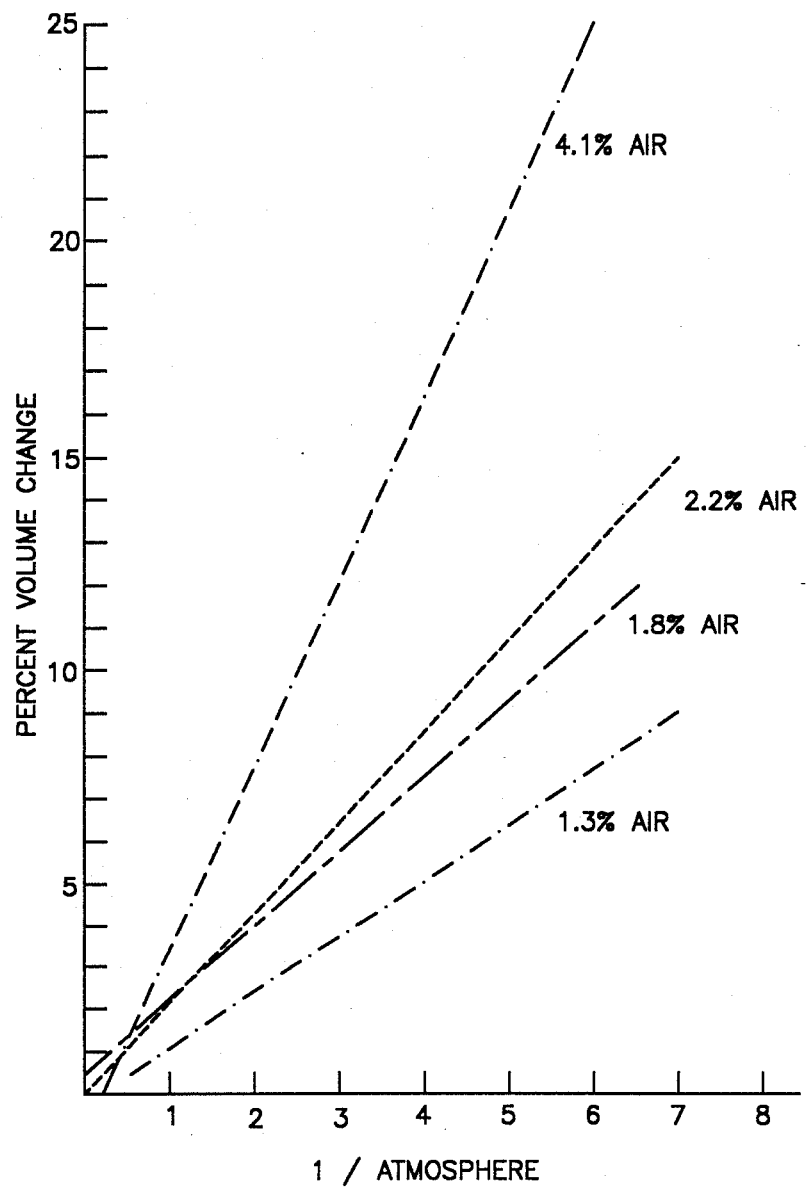
FIG. 6 is a graphical representation of the % volume change of fresh non-air entrained concrete having different air contents when subject to various degrees of vacuum according to this invention.
Figure 7:
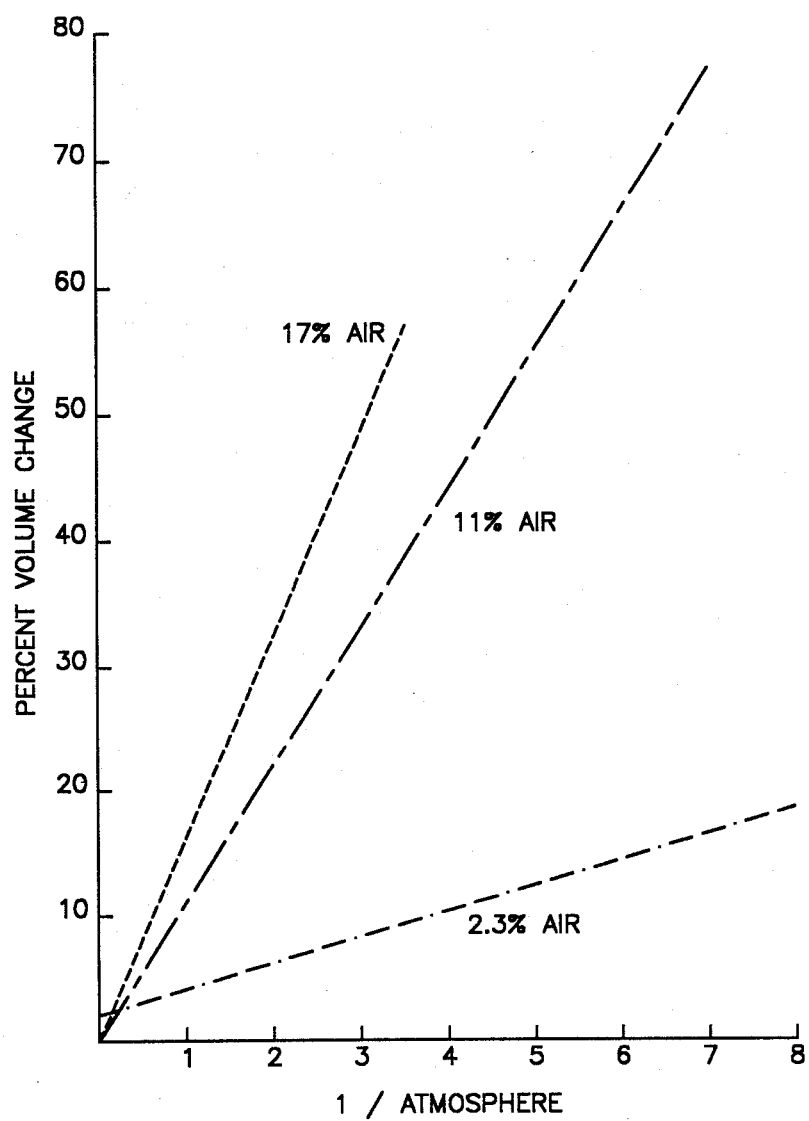
FIG. 7 is a graphical representation of the % volume change of fresh air entrained concrete having different air content when subject to various degrees of vacuum according to this invention.

The amount of air contained in the sample can also be easily calculated, as demonstrated by the graph in FIGS. 6 and 7.

In FIG. 6, the amount of expansion on four different samples of concrete, with different amounts of air, were measured and plotted as a function of vacuum. These are non-air entrained concrete samples. As can be seen in FIG. 6, the amount of expansion is directly proportional to the air content and inversely proportional to the absolute pressure. Thus the air content (since air is the only expansive component in concrete) can be quite accurately and repeatably determined merely be measuring the applied vacuum and resulting % expansion of the sample.

FIG. 7 shows a graph similar to FIG. 5, but utilizing air entrained concrete and mortar, where air is specifically entrained in the concrete. Again, the expansion is directly proportional to air content and inversely proportional to the absolute pressure.

As indicated above, the invention is not limited to determination of air in concrete, but has broader application. For example, it can be used to determine the amount of air or other gas entrained in asphalt.

ADVANTAGES OF USING VACUUM

Advantages of using vacuum instead of pressure to produce the measured volume change are:

1. A given vacuum will produce much greater volume change than will the same intensity of pressure.
2. Because of item #1, volume changes can be measured more accurately with vacuum because they are larger.
3. The meter is safer to use and can be made less sturdy for the following reasons:
   (a) It will be under less stress because of item #1.
   (b) A large margin of safety does not have to be designed into the chamber because the operator can never exceed 1 atm. with vacuum as he can with pressure.
   (c) If it shatters under stress, it will implode, which is safer than exploding.
4. Air meters using vacuum may need no clamps, which simplifies both manufacture and operation.
5. Vacuum facilitates the removal of unwanted air pockets.

While the invention has been described with some particularity, numerous modifications and adaptations can be made without departing from the scope of the invention.

What is claimed is:

1. A method of determining the relative amount of air entrained in a viscous building material comprising the steps of;
   providing a sample of said viscous material in a container,
   creating a vacuum in said container above said viscous material,
   and measuring the amount of expansion of the viscous material created by the expansion of the gas entrained therein at a given reduced pressure,
   whereby the amount of expansion is a function of the amount of gas entrained.

2. The invention as defined in claim 1, wherein said expansion is measured by measuring the change in electrical conductivity of the sample.

3. The invention as defined in claim 1, wherein the expansion is measured by measuring the physical change in position of one surface of the sample.

4. The invention as defined in claim 1, wherein means are provided to generate a signal proportional to the expansion of the sample, and means are provided to measure the change in said pressure.

5. The invention as defined in claim 4, wherein the signal is generated proportional to the unit electrical resistance of the material.

6. The invention as defined in claim 1, wherein a fluid is displaced responsive to the change in volume, and the displacement of the fluid is visually observed.

7. The invention as defined in claim 1, wherein the material is concrete.

8. The invention as defined in claim 7, wherein the sample is concrete with air entrained therein.

9. The invention as defined in claim 1 wherein the material is asphalt.

10. The invention as defined in claim 1 wherein the sample chamber is bottomless to enable pressing it into freshly placed concrete.

11. A method of determining the size distribution of voids caused by gas entrained in a material, comprising,
    placing a sample of the material in a container having at least a portion thereof transparent, creating a vacuum above said sample until all voids revealed through said transparent portion are visible to the eye, and measuring the sizes of the dilated voids and calculating the original void size from the dilated void size.

12. The invention as defined in claim 1, wherein the surface of the expanding sample is levelled off by its pressing against a horizontal surface.

13. A method of determining the relative amount of air entrained in a viscous building material comprising the steps of;

providing a sample of said viscous material in a container;

creating a vacuum in said container above said viscous material as a first parameter, thereby causing said viscous material to expand as a second parameter;

and measuring a given value of one of said parameters as a function of the other parameter;

whereby the amount of air entrained is determined by the value of said other parameter.

14. The invention as defined in claim 13 wherein the given value is the amount of vacuum, and the measured value is the expansion of the material.

15. The invention as defined in claim 13 wherein the given value is the amount of expansion and the measured value is the amount of vacuum.

* * * * *